United States Patent
Nutt et al.

[11] Patent Number: 5,204,328
[45] Date of Patent: Apr. 20, 1993

[54] PEPTIDES HAVING ATRIAL NATRIURETIC FACTOR ACTIVITY

[75] Inventors: Ruth F. Nutt, Green Lane; Stephen F. Brady, Philadelphia; Daniel F. Veber, Ambler; Theresa M. Williams, Harleysville, all of Pa.

[73] Assignee: Merck & Co., Inc., Rahway, N.J.

[21] Appl. No.: 789,378

[22] Filed: Nov. 5, 1991

Related U.S. Application Data

[63] Continuation of Ser. No. 543,621, Jun. 26, 1990, abandoned.

[51] Int. Cl.$^5$ .................... A61K 37/02; C07K 7/10
[52] U.S. Cl. .................... 514/13; 514/11; 514/12; 530/317; 530/324; 530/325; 530/326
[58] Field of Search .............. 530/317, 326, 325, 324; 514/11, 12, 13

[56] References Cited

FOREIGN PATENT DOCUMENTS

WO88/03537 5/1988 World Int. Prop. O. ......... 530/317

OTHER PUBLICATIONS

Stephenson S. et al., *Biochem. J.*, 243:183–187, 1987.
Baxter, J., et al., *Biotechnology*, 6:529–546, 1988.

*Primary Examiner*—Lester L. Lee
*Assistant Examiner*—Donna M. Fox
*Attorney, Agent, or Firm*—Robert J. North; Frank P. Grassler; Joseph F. DiPrima

[57] ABSTRACT

Atrial natriuretic factor analogs containing N-alkylated amino acids and showing enhanced potency and increased metabolic stability. These analogs have natriuretic, diuretic and vasorelaxant activity, making them suitable for treating congestive heart failure and renal hypertension.

13 Claims, No Drawings

PEPTIDES HAVING ATRIAL NATRIURETIC FACTOR ACTIVITY

Flynn et al., Biochem. Biophys. Res. Comm. 117 (3): 859-865 (1983), discloses a 28-amino acid peptide having the sequence

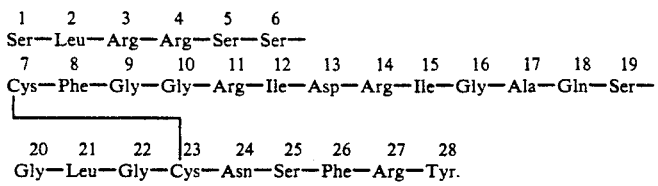

CONTINUING APPLICATION DATA

This is a continuation application of application Ser. No. 07/543,621, filed Jun. 26, 1990, now abandoned.

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action inplies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297-302, 1983) and atriopeptin (Currie et al., Science 111: 67, 1984).

Thibault et al., FEBS Lett. 164 (2): 286-290 (1983), discloses three peptides of 26, 31 and 33 amino acids and gives their amino acid composition but does not give any amino acid sequences. Since these peptides were isolated from rat atria, all optically active amino acids have L-configuration.

Since this peptide was isolated from rat atria, all optically active amino acids have L-configuration.

Currie et al., Science 223: 67-69 (1984), disclose two peptides having sequences 10-30 and 10-32 (numbering as above). Since these peptides were isolated from rat atria, all optically active amino acids have L-configuration.

Kangawa et al., Biochem. Biophys. Res. Comm. 118 (1): 131-139 (1984), disclose a 28-amino acid peptide having sequence 6-33 (numbering as above) having a methionine residue in lieu of isoleucine in 17-position. Since this peptide was isolated from atrial tissue, all optically active amino acids have L-configuration.

Thibault et al., FEBS Lett. 167 (2): 352-357 (1984), disclose isolation of a peptide of 103 amino acids and give the sequence of the C-terminal 73-amino acid fragment. The three peptides disclosed by Thibault et al., supra, correspond to C-terminal fragments of this peptide. Since all of these peptides were isolated from rat atria, and one that was synthesized conformed to the shortest one isolated, all optically active amino acids have L-configuration.

Misono et al., Biochem. Biophys. Res. Comm. 118 (2): 524-529 (1984), disclose isolation of a 25-amino acid peptide of sequence 9-33 (numbering as above). Since this peptide was isolated from rat atria, all optically active amino acids have L-configuration.

Needleman et al., U.S. Pat. No. 4,496,544, discloses isolation from several peptides of sequences 12-29, 12-30, 12-32, 12-33, 11-29, 11-30, 11-32, 11-33, 10-29, 10-30, 10-32 and 10-33 (numbering as above). Since all of these peptides were isolated from rat atria, all optically active amino acids have L-configuration.

Nutt et al., U.S. Ser. No. 51,981, describes various peptides having potent natriuretic activity, including those having the general formula:

X—Phe—B—C—Arg—Ile—F—Arg—Ile—I—J—Gln—Ser—M—Leu—O—Y

OBJECTS OF THE INVENTION

It is an object of the present invention to provide novel peptides having activity like that of ANF peptides isolated from biological materials. Another object is to provide novel peptides having potent natriuretic, vasodilatory and hypotensive activity. A further object is to provide novel peptides having enhanced metabolic stability. These and other objects of the present invention will be apparent from the following description.

SUMMARY OF THE INVENTION

The invention comprises peptides containing N-alkylated amino acids and having the following structure:

```
R—Cys—A—B—C—D—N—O—E
    |                       \
    |                        Ile
    |                       /
    Cys—J—Leu—I—Ser—H—G—F
    |
    K—L—M—P—Q
``` wherein
at least one residue is an N-alkylated amino acid,
R is H, Ac, Ser, Ser-Ser, Arg-Ser-Ser, Arg-Arg-Ser-Ser, or Ser-Leu-Arg-Arg-Ser-Ser;
A is Phe or NMePhe;
B is Gly, D/L-Ala or D/L-Pro;
C is Gly, L-Ala or D/L-Pro; or
B-C is $$\underset{HN}{\overset{D/L}{\phantom{X}}}\overset{(P)_n}{\underset{\underset{O}{\|}}{\phantom{X}}}\overset{R^1}{\underset{\underset{O}{\|}}{N}}\overset{D/L}{\phantom{X}}$$

where n=1 or 2, and $R^1$ is H or methyl;
D is Arg, NMeArg or D/L-Pro;
E is Arg, NMeArg or Pro;
F is Gly, D/L-Ala or D/L-Pro;
G is Ala, NMeAla or D/L-Pro, or F-G is $$\underset{HN}{\overset{D/L}{\phantom{X}}}\overset{(P)_n}{\underset{\underset{O}{\|}}{\phantom{X}}}\overset{R^1}{\underset{\underset{O}{\|}}{N}}\overset{D/L}{\phantom{X}}$$

where n=1 or 2, and $R^1$ is H or methyl;
H is Gln or D/L-Pro;
I is Gly, D/L-Ala or D/L-Pro;
J is Gly, D/L-Ala or D/L-Pro;
K is D/L-Asn, D/L-Pro or D/L-NMeAla;
L is D/L-Ser, or D/L-Pro;
M is D/L-Phe, D/L-NMePhe or D/L-Pro;
is Met, Ile, Leu or Nle;
O is Asp or Glu;
P is D/L-Arg, $NH_2$ or is absent; and
Q is D/L-Tyr, $NH_2$ or is absent.

The invention further comprises amides, lower alkyl esters and the physiologically acceptable metal salts and acid addition salts thereof.

The designation D/L represents both the D- and L-amino acid configuration. Unless otherwise indicated, all optically active amino acids have the L-configuration.

The foregoing peptides have properties similar to those of atrial natriuretic factor peptides isolated from biological materials, e.g., potent natriuretic, vasodilatory and hypotensive activity, but with increased potency and metabolic stability.

DETAILED DESCRIPTION OF THE INVENTION

The peptides of the present invention contain at least one N-alkylated amino acid which provides metabolic stability and includes high potencies. The presence of N-alkylated amino acids rigidifies peptide conformation and confers resistance towards enzymatic degradation of tertiary amide bonds.

Abbreviations for common amino acids are:

| Ala | Alanine | Leu | Leucine |
|---|---|---|---|
| Arg | Arginine | Lys | Lysine |
| Asn | Asparagine | Met | Methionine |
| Asp | Aspartic Acid | Phe | Phenylalanine |
| Cys | Cysteine | Pro | Proline |
| Glu | Glutamic Acid | Ser | Serine |
| Gln | Glutamine | Thr | Threonine |
| Gly | Glycine | Tyr | Tyrosine |
| His | Histidine | Val | Valine |
| Ile | Isoleucine | | |

Other abbreviations are:

| Nle | Norleucine |
|---|---|
| NMePhe | N-methyl phenylalanine |
| NMeArg | N-methyl arginine |
| NMeAla | N-methyl alanine |

Synthesis of these ANF analogs follows the protocol established for that of other ANF analogs, such as is described in R. F. Nutt and D. F. Veber, *Endocrinology and Metabolism Clinics of North America*, vol. 16, no. 1, March 1987, M. Rosenblatt, J. W. Jacobs, Eds., pp. 19-41. More preferred peptides are identified below.

Preferred peptides of the invention are those having the following sequence:

```
R—Cys—A—B—C—D—N—O—E
    |                       \
    |                        Ile
    |                       /
    Cys—J—Leu—I—Ser—H—G—F
    |
    K—L—M—P—Q
``` wherein
at least one residue is an N-alkylated amino acid,
R is H, Ac, Ser, Ser-Ser, Arg-Ser-Ser, Arg-Arg-Ser-Ser, or Ser-Leu-Arg-Arg-Ser-Ser;
A is Phe;
B is Gly or D-Ala;
C is Gly, L-Ala or D-Pro;
D is Arg, N-MeArg or L-Pro;
E is Arg;
F is Gly, L-Ala or D/L-Pro;
G is Ala, N-MeAla or Pro;
H is Gln;
I is Gly, D/L-Ala or L-Pro;
J is Gly, D/L-Ala or D-Pro;
K is D/L-Asn, D/L-Pro or D/L-N-MeAla;
L is D/L-Ser, D/L-Pro or D/L-N-/MeAla;
M is D/L-Phe, D/L-N-MePhe or D/L-Pro;
N is Met of Ile;
O is Asp or Glu;
P is D/L-Arg, $NH_2$ or is absent; and
Q is D/L-Tyr, $NH_2$ or is absent.

Tables 1, 2 and 3 identify examples of these potent analogs and their activity relative to sequence I shown below. Their structure is identified with reference to the following peptide sequence (I), which does not contain an N-methyl amino acid and which is therefore not within the scope of the invention.

```
 1           5                10
Ser Leu Arg Arg Ser Ser Cys Phe Gly Gly 15               20 (I)
Arg Ile Asp Arg Ile Gly Ala Gln Ser Gly
```

```
                              25              28
         Leu Gly Cys Asn Ser Phe Arg Tyr
```

Peptides of the invention may be prepared using solid phase synthesis, such as that described by Merrifield, *J. Am. Chem. Soc.*, 85, 2149 (1964) or other equivalent chemical syntheses known in the art such as the syntheses of Houghten, *Proc. Natl. Acal. Sci.*, 82, 5132 (1985), paying particular attention to treatment of the peptide-containing solution following HF cleavage. Solid-phase synthesis is commenced from the C-terminus of the peptide by coupling a protected amino acid to a suitable resin, as generally set forth in U.S. Pat. No. 4,244,946, issued Jan. 21, 1982 to Rivier et al., the disclosure of which is hereby incorporated by reference. Examples of synthesis of this general type are set forth in U.S. Pat. Nos. 4,305,872 and 4,316,891.

In synthesizing the polypeptides, the carboxyl terminal amino acid, having its alpha-amino group suitably protected, is coupled to a chloromethylated polystyrene resin or the like. After removal of the alpha-amino protecting group, as by using trifluoroacetic acid in methylene chloride for the t-Butyloxycarbonyl (Boc) group, the next step in the synthesis is ready to proceed. Other standard cleaving reagents and conditions for the removal of specific amino protecting groups may be used, as described in the open literature.

The remaining alpha-amino- and side-chain-protected amino acids are then coupled stepwise in the desired order by condensation to obtain an intermediate compound connected to the resin. As an alternative to adding each amino acid separately in the synthesis, some of them may be coupled to one another prior to the addition to the growing solid-phase chain. The selection of the appropriate coupling reagents is within the skill of the art.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris(dimethylamino)phosphonium hexafluorophosphate] method, N-hydroxysuccinic acid imido ester method, etc), Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

Common to chemical syntheses of peptides is the protection of the reactive side-chain groups of the various amino acid moieties with suitable protecting groups at the site until the group is ultimately removed after the chain has been completely assembled. Also common is the protection of the alpha-amino group on an amino acid or a fragment while that entity reacts at the carboxyl group followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the alpha- and omega-side chain amino groups are exemplified such as benzyloxycarbonyl (hereinafter abbreviated as Z), isonicotinyloxycarbonyl (iNOC), O-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl, (Boc), t-amyloxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified, for example, benzyl ester (OBzl), cyclohexyl ester (Chx), 4-nitrobenzyl ester (ONb), t-butylester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenylsulfonyl (Mts), and the like. The thiol group in cysteine may be protected with p-methoxybenzyl, triphenylmethyl, acetylaminomethyl, ethylcarbamoyle, 4-methylbenzyl, 2,4,6-trimethybenzyl (Tmb) etc., and the hydroxyl group in serine, threonine or tyrosine can be protected with benzyl, t-butyl, tetrahydropyranyl 2-bromobenzyloxycarbonyl, 2-6-dichlorobenzyl etc.

Stewart and Young, "Solid Phase Peptide Synthesis", Pierce Chemical Company, Rockford, Ill. (1984) provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino-acid sequence has been completed, the intermediate peptide is removed from the resin support by treatment with a reagent, such as liquid HF and one or more cation scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Alternately, the acetic acid solution containing peptide is oxidized to the disulfide containing product using I$_2$ as the oxidizing agent.

TABLE 1

| | Structure | | Vasorelaxant Relative Potency Rabbit Renal Artery | Aorta |
|---|---|---|---|---|
| | I Flynn et al. | (1-28) | 1 | 1 |
| | I Flynn et al. | (3-28) | 1 | 1 |
| 1 | D—Ala(9, 22) Ala(10, 16) Pro(20) | (3-28) | 3.3 | |
| 2 | D—Ala(9) Ala(10, 16) Pro(20) | (3-28) | 1.97 | |
| 3 | D—Ala(9) Ala(16) Pro(20) | (3-28) | 1.52 | |
| 4 | D—Ala(9) Ala(10) Pro(11) | (3-28) | 0.38 | |
| 5 | D—Ala(9) Pro(11) | (3-28) | 1.48 | |
| 6 | D—Ala(9) Pro(10) | (3-28) | 0.73 | |
| 7 | N—MePhe(8) | (3-28) | 0.13 | |
| 8 | Pro(11) | (3-28) | 0.3 | |
| 9 | Pro(12) | (3-28) | 0.12 | |
| 10 | Pro(13) | (3-28) | | 0.19 |
| 11 | Pro(14) | (3-28) | 0.28 | |
| 12 | Pro(15) | (3-28) | 0.008 | |
| 13 | Pro(16) | (3-28) | | 0.30 |
| 14 | D—Pro(16) | (3-28) | | 0.53 |
| 15 | N—MeAla(17) | (3-28) | 0.81 | |
| 16 | Pro(18) | (3-28) | 0.25 | |
| 17 | Pro(20) | (3-28) | 1.5 | |
| 18 | Pro(21) | (3-28) | 0.028 | |
| 19 | Pro(22) | (3-28) | | 0.19 |
| 20 | D—Pro(22) | (3-28) | 0.3 | |
| 29 | [structure] (21, 22) | (3-28) | 0.15 | |
| 30 | [structure] (9, 10) | (3-28) | 0.06 | |
| 31 | [structure] (9, 10) | (3-28) | 0.096 | |
| 32 | [structure] (9, 10) | (3-28) | 0.107 | |

TABLE 2

| | Structure | | Vasorelaxant Relative Potency Rabbit Renal Artery |
|---|---|---|---|
| | I Flynn et al. | (7-27)-NH$_2$ | 1 |
| 21 | Pro(24) | (7-27)-NH$_2$ | 1.3 |
| 22 | Pro(25) | (7-27)-NH$_2$ | 0.24 |
| 23 | Pro(26) | (7-27)-NH$_2$ | 3.86 |

TABLE 3

| | Structure | | Vasorelaxant Relative Potency Aorta |
|---|---|---|---|
| | I Flynn et al. | (5-26)-NH$_2$ | 1 |
| 24 | Pro(9) | (5-26)-NH$_2$ | 0.05 |
| 25 | D-Pro(9) | (5-26)-NH$_2$ | 0.004 |
| 26 | Pro(10) | (5-26)-NH$_2$ | 0.05 |
| 27 | D-Pro(10) | (5-26)-NH$_2$ | 0.39 |
| 28 | D-Pro(20) | (5-26)-NH$_2$ | 0.16 |

Structure 1 represents a peptide sequence of amino acids 3 through 28 of formula I with D-Ala at positions 9 and 22, Ala at positions 10 and 16 and Pro at position 20. Structure 26 represents a peptide sequence of amino acids 7–27 of formula I with Pro at position 26 and an amino terminal amino group following Arg (27).

More preferred peptides of the invention are those identified as structures 1, 2, 3, 5, 6, 14, 15, 17, 21 and 23.

EXAMPLE 1

PROLINE-26 ANF (7–27) amide

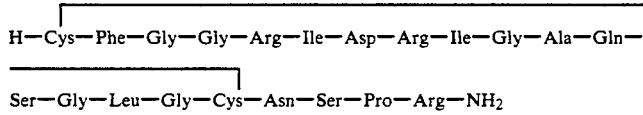

H—Cys—Phe—Gly—Gly—Arg—Ile—Asp—Arg—Ile—Gly—Ala—Gln—Ser—Gly—Leu—Gly—Cys—Asn—Ser—Pro—Arg—NH$_2$

Fully-protected resin-bound precursor was assembled, using manufacturer-supplied reagents and protocols throughout, in 0.5-mmole quantity on an Applied Biosystems Model 430A Peptide Synthesizer. Thus, sidechain functionality-protected residues Cys (para-methylbenzyl), Arg (N$^G$-tosyl), Asp (beta-benzyl), Ser (benzyl), and other sidechain-non-protected residues were introduced stepwise by double treatment during each cycle with the appropriate activated Boc amino acid, starting with 1% cross-linked beta-methylbenzhydrylamine resin. The resin-bound peptide (2.80 g.) was mixed with 5 ml. of anisole and cleaved with approx. 50 ml. of liquid HF in a Kel-f apparatus at 0°–5° for 1.5 hours. After removal of the HF by evaporation, ether was added to the residue to precipitate crude peptide, which was isolated by filtration of the spent resin/peptide mixture and drying in vacuo.

The solid was leached with a total of 200 ml. of 2N acetic acid in several portions, and to the leachate was added a solution of 1.46 g. of iodine in 450 ml. of glacial acetic acid. After 2½ hours 2.11g. of zinc dust was added to the ice-cooled solution, with stirring for 1–2 minutes (decolorized), followed by filtering and removal of solvent under vacuum to give a yellow residue which was charged to a column approximately 5×90 cm. of Sephadex G50F packed and eluted with 50% acetic acid. Fractions containing product by TLC and HPLC were pooled for concentration and lyophilization (yield 540 mg.) Product was purified by preparative HPLC (0.1% trifluoroacetic acid/acetonitrile-water gradient) to give fractions yielding 348 mg. of final product upon concentration and lyophilization, ca. 97% pure by HPLC [data: amino acid analysis, 360 MHz PMR, FAB-MS].

Assembly of other peptides within the present invention, while not specifically exemplified, is within the ordinary skill of an artisan.

Therapy

The peptides of the invention are potent diuretic, natriuretic, vasorelaxant, hypotensive, and anti-hypertensive agents and are useful in the treatment of pathological conditions associated with water and/or electrolyte imbalances as well as in hypertension, especially in renovascular hypertension. They are substantially non-toxic and have the added advantage of providing the desired effects at very low dosage levels. Although the compounds themselves are water-soluble at the very low concentrations at which they are usually employed, they are preferably used in the form of their freely water-soluble acid addition salts with pharmaceutically acceptable acids, e.g. acetic, citric, malic, or succinic acid. The acetate salts are particularly advantageous because they are easily obtained as the products of the synthesis process described above. Such freely water-soluble salts may be converted, if desired, into different acid addition salts with pharmaceutically acceptable acids, by treatment with the appropriate ion exchange resin in the manner described by Boissonas et al., 1960 Helv. Chim. Acta 43, 1349. Suitable ion exchange resins are strongly basic anion exchange resins, for example those listed in Greenstein and Winitz "Chemistry of the Amino Acids", John Wiley & Sons, Inc., New York and London 1961, vol, 2, p. 1456. Basically substituted cross-linked polystyrene resins such as Amberlite IRA-400 or IRA-410 are preferred. Freely water-soluble salts of the peptides of this invention may also be converted to salts of low solubility in body fluids by treatment with a slightly water-soluble pharmaceutically acceptable acid, e.g. tannic or pamoic acid. In general, the acid addition salts of the peptides of this invention with pharmaceutically acceptable acids are biologically fully equivalent to the peptides themselves.

When the peptides of this invention or their acid addition salts with pharmaceutically acceptable acids are employed in medicine they are administered systemically, either by intravenous, subcutaneous, or intramuscular injection, or by sublingual or nasal administration, in compositions in conjunction with pharmaceutically acceptable vehicles or carriers. For administration by injection or by the nasal route it is preferred to use the peptides in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of pharmaceutically acceptable surface-active agents to ensure rapid absorption of the respective peptides by the nasal mucosa. For sublingual administration it is preferred to formulate the peptides of this invention as rapidly dissolving tablets together with solid excipients or carriers such as lactose. Examples of such excipients or carriers are found in standard pharmaceutical texts, e.g. in Remington's Pharmaceutical Sciences, Mack Publishing Company, Easton, Pa. 1970. Intranasal or sublingual administration may be less precise than intravenous injection but it may be a more convenient form of treatment.

When administration of the peptides of this invention is desired for the obtention of diuretic, natriuretic, vasorelaxant, hypotensive, of anti-hypertensive effects such as for example in the treatment of hypertension, in particular of renovascular hypertension, the dosage to be administered will depend upon such factors as the species, age, weight, sex, and condition of the patient, and with the chosen form of administration. Generally, treatment is initiated with small dosages substantially less than the optimal dose of the respective peptide. Thereafter, the dosage is increased by small increments until the optimal effect under the given circumstances is reached. In general, the peptides of this invention are most desirably administered at dosage levels which will give effective concentrations of the respective peptides in the blood of the patient without causing any harmful or deleterious side effects, and preferably at a level which is in the range from about 0.01 mcg to about 100 mcg per kilogram body weight, although as aforementioned variations will occur. However, a dosage level which is in the range of from about 0.1 mcg to about 25 mcg per kilogram body weight is most desirably employed to achieve effective results.

It is often desirable to administer the peptides of this invention continuously over prolonged periods of time, and one way by which this may be achieved is by administration of long-acting, slow-release, or depot dosage forms. Such dosage forms may either contain a pharmaceutically acceptable salt of the respective peptide having a low degree of solubility in body fluids, for example the tannic or pamoic acid salts described above, or they may contain the peptides in the form of a water-soluble salt thereof together with a protective carrier which prevents rapid release. In the latter case, for example, the peptides may be formulated with a non-antigenic, partially hydrolyzed gelatin in the form of a viscous liquid; or the peptides may be adsorbed on a pharmaceutically acceptable solid carrier, for example zinc hydroxide, and may be administered in suspension in a pharmaceutically acceptable liquid vehicle; or the peptides may be formulated in gels or suspensions with a protective non-antigenic hydrocolloid, e.g. sodium carboxymethylcellulose, polyvinylpyrrolidone, sodium alginate, gelatine, polygalacturonic acids, for example pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the peptides of this invention may also be obtained by microencapsulation in a pharmaceutically acceptable coating material, for example, gelatine, polyvinyl alcohol, or ethyl cellulose. Further examples of coating materials and of the processes used for microencapsulation are described by J. A. Herbig in Encyclopedia of Chemical Technology, vol. 13, 2nd Ed., Wiley, New York 1967, p, 436 ff. The peptides of this invention may advantageously also be formulated in poly(d,l-lactide) microspheres such as described, e.g., in U.S. Pat. No. 3,773,919 or by Benita et al., 1984 J. Pharm. Sci. 73, 1721, or they may be microencapsulated in lactic-glycolic acid polymers as described in "Lactic-Glycolic Acid Polymers in Drug Carriers in Biology and Medicine", D. L. Wise et al., Eds., Academic Press, Orlando, Fla. 1979. Controlled slow-release preparations of the peptides may also be obtained by formulating them with the new microporous polyproplyene polymers as described by Kruisbrink et al., 1984 J. Pharm. Sci. 73, 1713. Alternatively, the peptides of this invention may also be formulated for controlled long-term release in synthetic liposomes such as described, e.g., by Gregoriadis, 1976 New Engl. J. Med. 295, 704 and ibid. 756. All the above preparations for controlled long-term release are designed to release from about 0.01 to about 25 mcg per kilogram body weight per day and are preferably administered by intramuscular injection. Some of the solid dosage forms of the peptides of this invention described above, for example some of the sparingly water-soluble salts thereof, or dispersions in or adsorbates on solid carriers therefor, for example dispersions in a neutral hydrogel of a polymer of ethylene glycol methacrylate or similar monomers crosslinked as described in U.S. Pat. No. 3,551,556, may also be formulated in the form of pellets releasing about the same amounts of peptides as shown above and may be implanted subcutaneously or intramuscularly. Furthermore, sterile aqueous solution of the peptides of this invention containing preservatives and other solutes so as to make them isotonic may also be administered intravenously in a continuous manner by means of a minipump attached to the body of the patient, or said minipump may be governed by the action of a sensor attached to or implanted in the body of the patient which activates the minipump whenever the blood pressure of the patient or the concentration of Na+ in his bloodstream exceed a certain predetermined safe limit. Conjugates of the peptides of this invention with albumin are also useful as long-acting dosage forms thereof.

What is claimed is:

1. A peptide having the amino acid sequence:

```
R—Cys—A—B—C—D—N—O—E
    |                   \
    |                    Ile
    |                   /
    Cys—J—Leu—I—Ser—H—G—F
    |
    K—L—M—P—Q
``` wherein
R is H, Ac, Ser, Ser-Ser, Arg-Ser-Ser, Arg-Arg-Ser-Ser, or Ser-Leu-Arg-Arg-Ser-Ser;
A is Phe or N-MePhe;
B is Gly, D/L-Ala or D/L-Pro;
C is Gly, L-Ala or D/L-Pro; or
B-C is where
n=1 or 2, and
$R^1$ is H or methyl;
D is Arg, N-MeArg or D/L-Pro;
E is Arg, N-MeArg or Pro;
F is Gly, D/L-Ala or D/L-Pro;
G is Ala, N-MeAla or D/L-Pro, or
F-G is wherein
n=1 or 2, and
$R^1$ is H or methyl;
H is Gln or D/L-Pro;
I is Gly, D/L-Ala or D/L-Pro;
J is Gly, D/L-Ala or D/L-Pro;
K is D/L-Asn, D/L-Pro or D/L-N-MeAla;
L is D/L-Ser, D/L-Pro or D/L-N-MeAla;
M is D/L-Phe, D/L-N-MePhe or D/L-Pro;
N is Met, Ile, Leu or Nle
O is Asp or Glu;
P is D/L-Arg, NH2 or is absent;
Q is D/L-Tyr, NH2 or is absent;
with the proviso that one residue of said peptide shall be N-methylated, said N-methylated residue taken from the group consisting of N-MePhe at position A, N-MeArg at position D, N-MeArg at position E, N-MeAla at position G, D/L-N-MeAla at position K, D/L-N-MeAla at position L and D/L-N-MePhe at position M;
with the additional proviso that, when all other residue positions are identical to native ANP, M is not N-MePhe, K is not Pro or C is not Pro.

2. A peptide of claim 1 having the following sequence:

```
R—Cys—A—B—C—D—N—O—E
    |                   \
    |                    Ile
    |                   /
    Cys—J—Leu—I—Ser—H—G—F
    |
    K—L—M—P—Q
``` wherein
R is H, Ac, Ser, Ser-Ser, Arg-Ser-Ser, Arg-Arg-Ser-Ser, or Ser-Leu-Arg-Arg-Ser-Ser;
A is Phe;
B is Gly or D-Ala;
C is Gly, L-Ala or D-Pro;
D is Arg, N-MeArg or L-Pro;
E is Arg;
F is Gly, L-Ala or D/L-Pro;
G is Ala, N-MeAla or Pro;
H is Gln;
I is Gly, D/L-Ala or L-Pro;
J is Gly, D/L-Ala or D-Pro;
K is D/L-Asn, D/L-Pro or D/L-N-MeAla;
L is D/L-Ser, D/L-Pro or D/L-N-MeAla;
M is D/L-Phe, D/L-N-MePhe or D/L-Pro;
N is Met or Ile;
O is Asp or Glu;
P is D/L-Arg, NH2 or is absent; and
Q is D/L-Tyr, NH2 or is absent.

3. A method of treating a disorder of electrolyte balance which comprises administering to a mammalian species a therapeutically active amount of a peptide of claim 1.

4. A method of lowering hypertension which comprises administering to a mammalian species a therapeutically active amount of a peptide of claim 1.

5. The peptide as claimed in claim 1, wherein A is N-MePhe.

6. The peptide as claimed in claim 1, wherein $R^1$ in B-C is methyl.

7. The peptide as claimed in claim 1, wherein D in N-MeArg.

8. The peptide as claimed in claim 1, wherein E is N-MeArg.

9. The peptide as claimed in claim 1, wherein G is N-MeAla.

10. The peptide as claimed in claim 1, wherein R¹ in F-G is methyl.

11. The peptide as claimed in claim 1, wherein K is D/L-N-MeAla.

12. The peptide as claimed in claim 1, wherein L is D/L-N-MeAla.

13. The peptide as claimed in claim 1, wherein M is D/L-N-MePhe.

* * * * *